(12) United States Patent
Ty et al.

(10) Patent No.: US 11,589,847 B2
(45) Date of Patent: Feb. 28, 2023

(54) FASTENING DEVICE FOR ACQUIRING BONE MARROW ASPIRATE

(71) Applicant: Beacon Biomedical, LLC, Jupiter, FL (US)

(72) Inventors: Dennis Ty, Jupiter, FL (US); Dale Mitchell, Jupiter, FL (US)

(73) Assignee: BEACON BIOMEDICAL, LLC, Jupiter, FL (US)

( * ) Notice: Subject to any disclaimer, the term of this patent is extended or adjusted under 35 U.S.C. 154(b) by 400 days.

(21) Appl. No.: 16/803,602

(22) Filed: Feb. 27, 2020

(65) Prior Publication Data

US 2020/0268361 A1    Aug. 27, 2020

Related U.S. Application Data (60) Provisional application No. 62/811,017, filed on Feb. 27, 2019.

(51) Int. Cl.
*A61B 10/02*    (2006.01)

(52) U.S. Cl.
CPC .... *A61B 10/025* (2013.01); *A61B 2010/0258* (2013.01)

(58) Field of Classification Search
CPC ................................................ A61B 10/025
See application file for complete search history.

(56) References Cited

U.S. PATENT DOCUMENTS

| | | | |
|---|---|---|---|
| 2,219,605 A * | 10/1940 | Turkel | A61B 10/025 604/164.01 |
| 5,098,435 A | 3/1992 | Stednitz et al. | |
| 5,279,306 A * | 1/1994 | Mehl | A61B 10/025 600/566 |
| 6,312,394 B1 * | 11/2001 | Fleming, III | A61B 10/025 600/567 |
| 9,913,929 B2 | 3/2018 | Assell | |
| 2002/0040228 A1 * | 4/2002 | Freier | A61B 10/025 606/167 |
| 2004/0010236 A1 | 1/2004 | Morawski et al. | |
| 2007/0293788 A1 * | 12/2007 | Entrekin | A61B 10/025 600/564 |
| 2009/0105775 A1 | 4/2009 | Mitchell et al. | |
| 2014/0066758 A1 | 3/2014 | Marik et al. | |

FOREIGN PATENT DOCUMENTS

| | | |
|---|---|---|
| CN | 204169875 | 2/2015 |
| WO | WO2010091368 | 8/2010 |
| WO | WO2011054124 | 5/2011 |

* cited by examiner

*Primary Examiner* — Christian A Sevilla
(74) *Attorney, Agent, or Firm* — McHale & Slavin, P.A.

(57) ABSTRACT

The invention involves a device and method for acquiring bone marrow aspirate. The system includes an elongated cannulated fastener having a threaded end for attachment to a bone. The threaded portion includes a directional aperture sized to allow marrow to be drawn into the cannula. The directional aperture also allows the user to direct the aperture in a desired direction within the bone for acquisition of the marrow. The distal end of the cannulated fastener includes a connector which may be in the form of a Luer lock to allow vacuum to be applied to the cannula for drawing the marrow into a syringe or the like.

17 Claims, 11 Drawing Sheets

FASTENING DEVICE FOR ACQUIRING BONE MARROW ASPIRATE

FIELD OF INVENTION

The present invention generally relates to surgical procedures requiring bone graft; and more particularly, to a surgical fastener and method for securing a surgical fixture and acquiring bone marrow aspirate.

BACKGROUND INFORMATION

In the U.S., bone grafts are most commonly used in spine fusion surgery and, more generally, in the fusion or arthrodesis of any skeletal joint to bridge a gap between bone segments, and may also provide a three-dimensional scaffold on which the bone can grow.

In addition, bone graft may be used in trauma surgery for the treatment of fresh fractures and non-unions where the bone has been shattered, or where the patient is at a very high risk of developing a non-union fracture.

Joint reconstruction and revision surgery is another area where a patient is likely to need a bone graft because a large void may result from the removal of the original joint or implant.

There are different types of bone graft materials that may be used to assist a patient's body in bone regeneration. These bone graft materials are typically classified as either natural or synthetic materials.

Natural bone graft materials are classified in the following groups. Autograft is bone graft material that is obtained from the same individual that will receive the bone graft material. Allograft is bone graft material that is obtained from another human source, which typically is from cadavers. Xenograft is bone graft material that is obtained from another species.

Bone grafts can also be categorized by their bone-forming properties as osteoconductive, osteoinductive or osteogenic. Osteoconductivity is the ability of a material to provide an appropriate scaffold or matrix upon which new bone tissue can form. Osteoinductivity is the ability of a material to stimulate the patient's own system to form new bone. Osteogenic material generates new bone tissue itself. Osteoblasts, which can be found in bone marrow and mesenchymal cells, are the only cells that can create new bone.

Autograft bone has historically been the standard of care because of its osteoconductive, osteoinductive and osteogenic properties. At the time of surgery, bone is taken from a donor site in the patient, often the iliac crest bone, but others are used, and is then re-implanted back into the patient at the surgical site.

However, autograft is often not used because obtaining the graft generally requires a second surgical procedure with associated risks and expenses. In addition, the autograft may also result in significant post-operative issues, most significantly pain.

Therefore, what is needed in the art is a device and method of acquiring bone marrow aspirate that does not require a second surgical site. The device through which the bone marrow aspirate is acquired should provide additional function in the procedure, wherein acquiring the bone marrow aspirate is an additional feature provided by the device. The device should be simple to operate and quickly assembled, requiring minimal tools. Moreover, the device should assemble and function in such a way as to not distract or obstruct the surgeon from completing the surgery.

Thus, the present invention provides a device and method of acquiring bone marrow aspirate which overcomes the disadvantages of prior art bone marrow acquiring systems. The fastener and bone marrow acquisition device of the present invention not only provides for relative ease of use, it also permits the securement of surgical fixtures without the need of additional fasteners. The present invention also provides a tip suitable for boring pilot holes into bone, thereby eliminating or reducing the need for Jamshidi needles and Kirshner wires.

SUMMARY OF THE INVENTION

Briefly, the invention involves a device and method for acquiring bone marrow aspirate. The system includes an elongated cannulated fastener having a threaded end for attachment to a bone. The threaded portion includes a directional aperture sized to allow marrow to be drawn into the cannula. The directional aperture also allows the user to direct the aperture in a desired direction within the bone for acquisition of the marrow. The distal end of the cannulated fastener includes a connector which may be in the form of a Luer lock to allow vacuum to be applied to the cannula for drawing the marrow into a syringe or the like.

Accordingly, it is an objective of the present invention to provide a cannulated fastener constructed to temporarily attach a surgical fixture to a bone while extending outside of the patient's anatomy.

It is a further objective of the present invention to provide a cannulated fastener constructed and arranged to temporarily secure a surgical device to a bone, while allowing bone marrow to be acquired from the attachment site.

It is yet a further objective of the present invention to provide a cannulated fastener that can be rotated to directionally acquire marrow.

It is another objective of the present invention to provide a cannulated fastener that includes an attachment on a distal end thereof to provide vacuum to the cannula.

Other objectives and advantages of this invention will become apparent from the following description taken in conjunction with the accompanying drawings wherein are set forth, by way of illustration and example, certain embodiments of this invention. The drawings constitute a part of this specification, include exemplary embodiments of the present invention, and illustrate various objects and features thereof.

DETAILED DESCRIPTION OF THE PREFERRED EMBODIMENTS

While the present invention is susceptible of embodiment in various forms, there is shown in the drawings and will hereinafter be described a presently preferred embodiment, with the understanding that the present disclosure is to be considered an exemplification of the invention and is not intended to limit the invention to the specific embodiments illustrated.

Referring generally to FIGS. 1-13, a cannulated fastener 100 and method of use for securing a surgical fixture and withdrawing bone marrow from the bone puncture is illustrated. The cannulated fastener includes a first end 10 which includes a moil drill point 14, a tapered lead 16, threads 12, and a directional aperture 18. The second or distal end 20 includes a connector 22, a shoulder 24 and a spacer zone 26. The moil drill point 14 is polygonal in shape, having a center point 28 and multiple sharp edges 30. The center point 28 allows the cannulated fastener to be inserted through tissue and bone without a pilot hole. The location of the center point 28 provides the user with a positive location once the center point 28 contacts bone, and resists walking of the point across the surface of the bone, as is commonly seen with points, such as a trocar point which positions the point to one side. The center point 28 also allows the use of mallets and the like to propel the point through the outer surface of the bone. Still yet, the moil drill point 14 provides a closed first end to the cannulated fastener 100. It should be noted that split drill points, spade points and other points that include a center point may be utilized without departing from the scope of the invention. The tapered lead 16 extends between the moil drill point 14 and the threads 12. In general, the tapered lead 16 is constructed and arranged to expand the diameter of the hole created by the moil drill point 14 and smooth or burnish the sidewalls, while sizing the formed hole for compressive thread forming into the bone. In this manner, threads are formed in the bone without loose bone chips, which may cause various issues during or after the surgical procedure. Thus, the surface of the tapered lead 16 is smooth and free from cutting surfaces. The threads 12 may be single, double, triple or more helix; the additional helix providing insertion into a bone with fewer rotations. The threads 12 are generally constructed to allow the cannulated fastener to be securely fastened to the bone. The threads 12 also allow the user to precisely rotate the directional aperture 18 for control of the depth and direction from which the bone marrow is drawn from the bone. It should also be noted that while threads are the preferred embodiment, other holding surfaces may be utilized without departing from the scope of the invention such holding surfaces may include, but should not be limited to, knurling, annular rings, surface finish of the outer surface, coatings or the like may be utilized in place of or in conjunction with the threads to hold the cannulated fastener 100 suitably to the bone. The directional aperture 18 is positioned within the threaded area 32. The directional aperture 18 is cut through the side of the cannulated fastener 100 to the cannula bore 34, which extends from behind the center point 28 to the distal end 20. The directional aperture 18 is preferably oval in shape, but may take any shape suitable for drawing marrow or marrow aspirate from a bone. It should also be noted that a plurality of directional apertures may alternatively be utilized without departing from the scope of the invention. The cannula 36 extends through the threaded portion 32 to the distal end 20, terminating in a connector 22. The connector 22 may be welded, formed or overmolded to the cannula 36 to create an airtight connection therebetween. The connector 22 preferably includes a luer lock 38, and may also include threads 40, illustrated herein as ACME threads. It should be noted that other thread forms suitable for securing the connector to a source of vacuum may be substituted for the ACME threads without departing from the scope of the invention. The connector 22 also includes a shoulder 24 arranged to be substantially perpendicular to the cannula 36. In this manner, the shoulder 24 can be utilized to contact an adjacently placed surface of a surgical fixture to retain the fixture's positioning. A spacer zone 26 is positioned between the shoulder 24 and the connector threads 40 to allow the vacuum source to be connected to the threads for marrow extraction, while the shoulder 24 is simultaneously utilized to retain a surgical fixture. Thus, the cannula 36 is preferably constructed from a suitable metal such as stainless steel, while the connector 22 is constructed from a suitable plastic or metal.

Referring to FIGS. 6-13, the cannulated fastener 100 is illustrated as securing a surgical fixture 50 in position on a bone structure 52 for a surgical procedure. In this particular illustration, the bone structure 52 is a human pelvis bone 54. It should be noted that the present invention is suitable for use on all bones of mammals having suitable size for connection thereto without departing from the scope of the invention. As illustrated, the shoulder 24 cooperates with a surface 56 of the surgical fixture 50 to retain the positioning of the surgical fixture.

Figure 1:
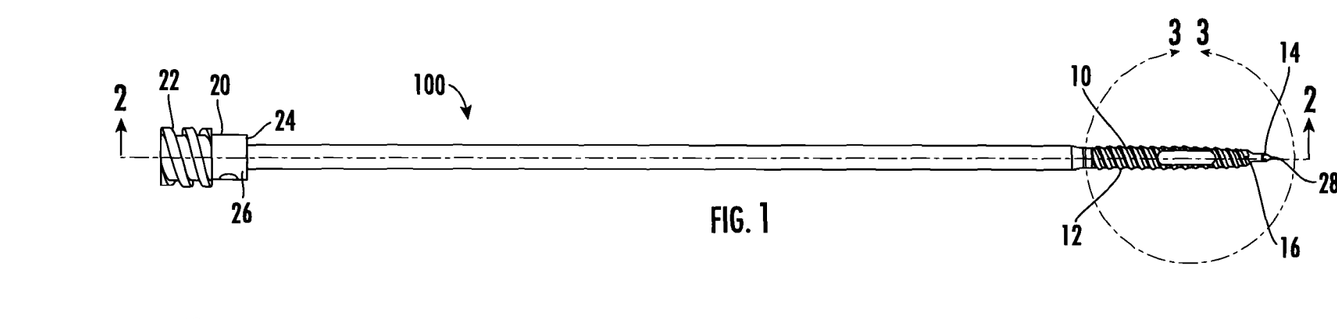
FIG. 1 is a side view of one embodiment of the present invention.
Figure 2:
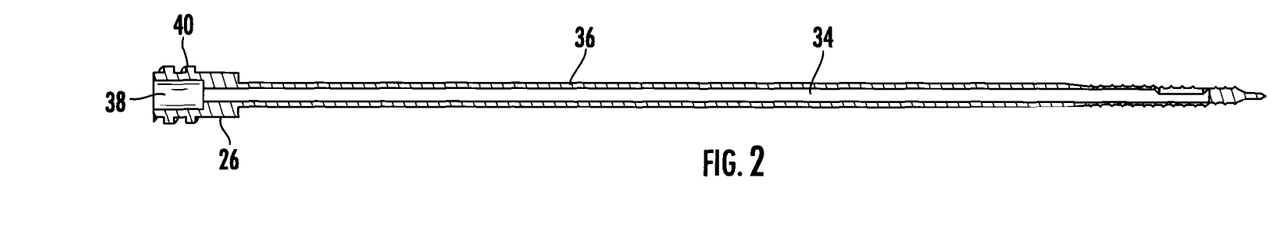
FIG. 2 is a section view of the embodiment shown in FIG. 1, taken along lines 2-2, illustrating the fastening cannula and the directional aperture.
Figure 3:
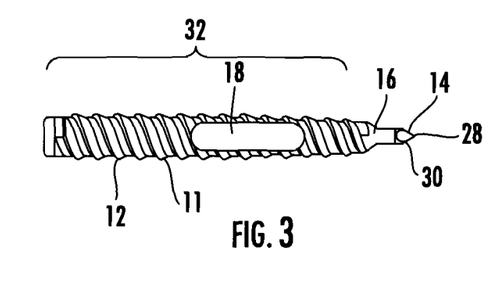
FIG. 3 is a partial top side view taken along lines 3-3 of FIG. 1, illustrating the directional aperture.
Figure 4:
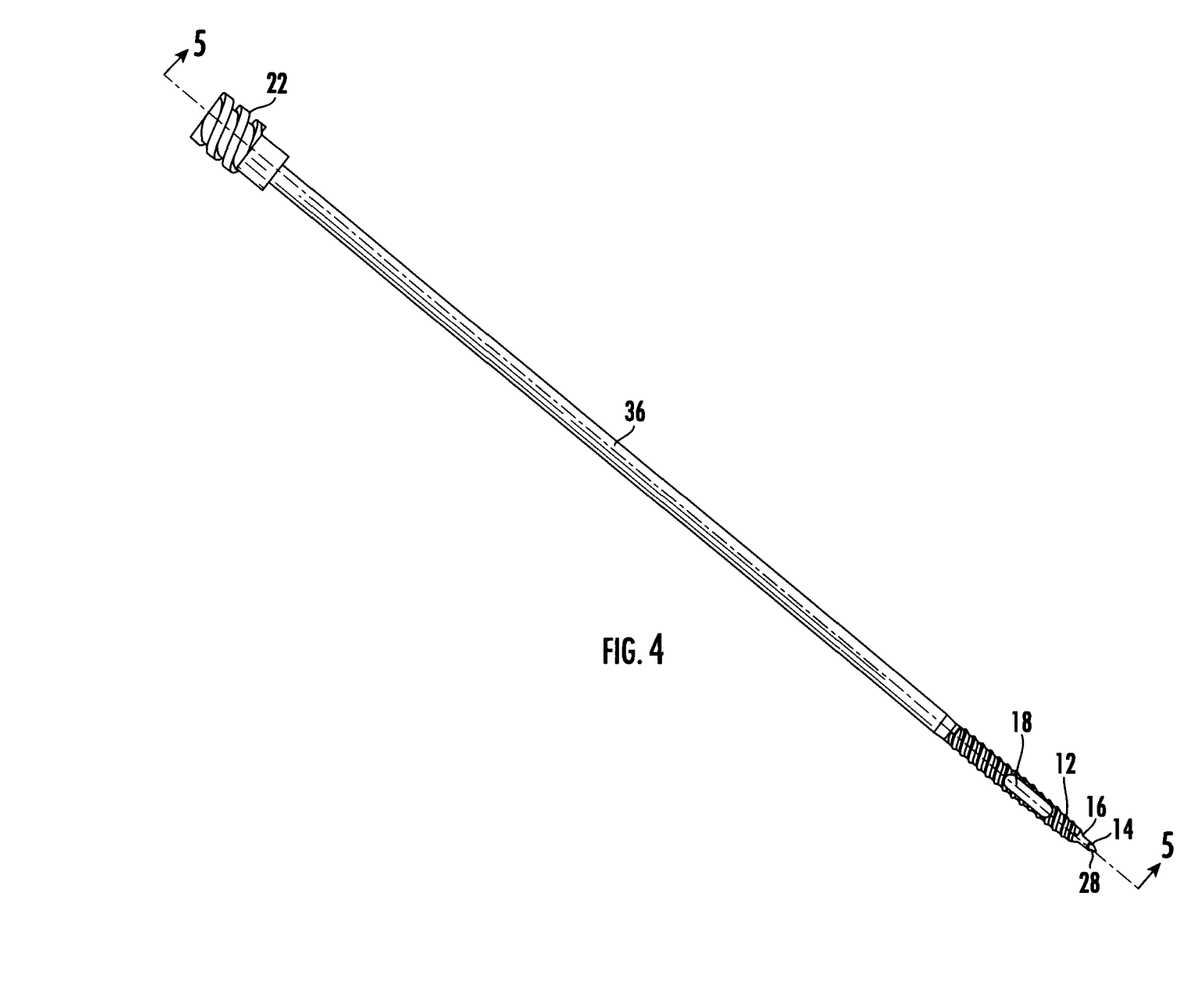
FIG. 4 is a perspective view of the fastening cannula of the present invention.
Figure 5:
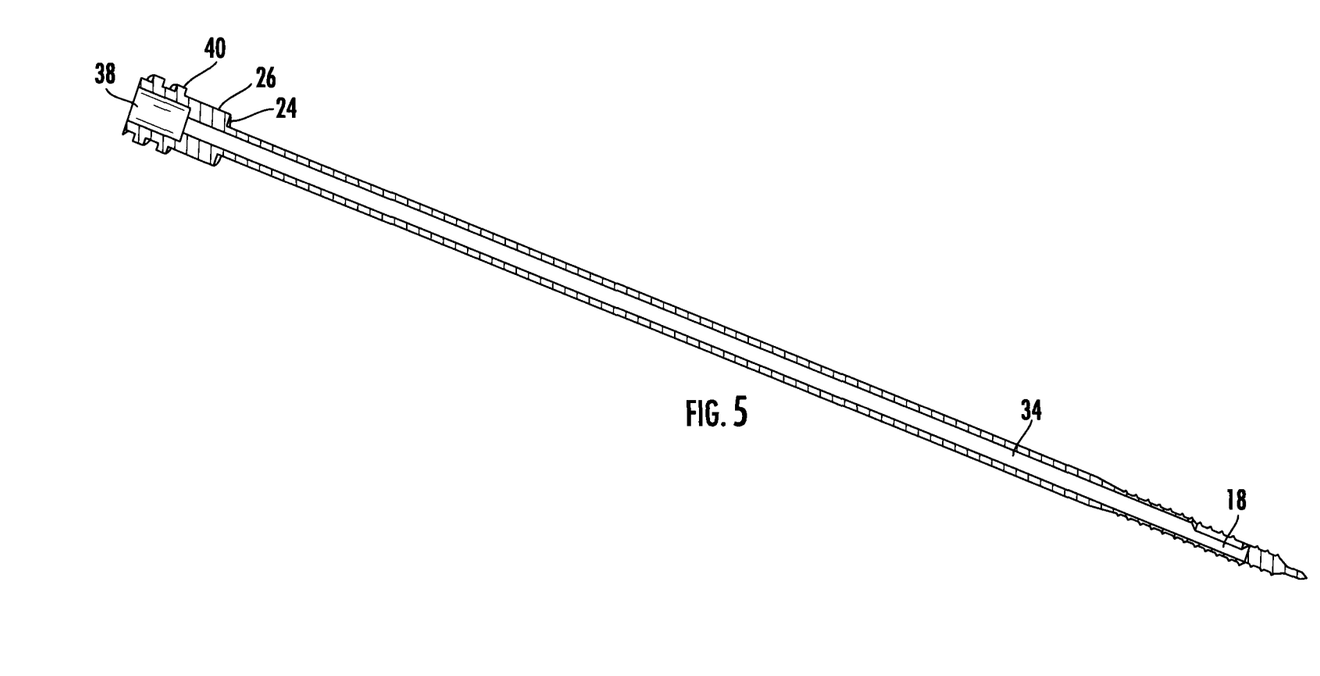
FIG. 5 is a section view taken along lines 5-5 of FIG. 4, illustrating the internal construction of the fastening cannula.
Figure 6:
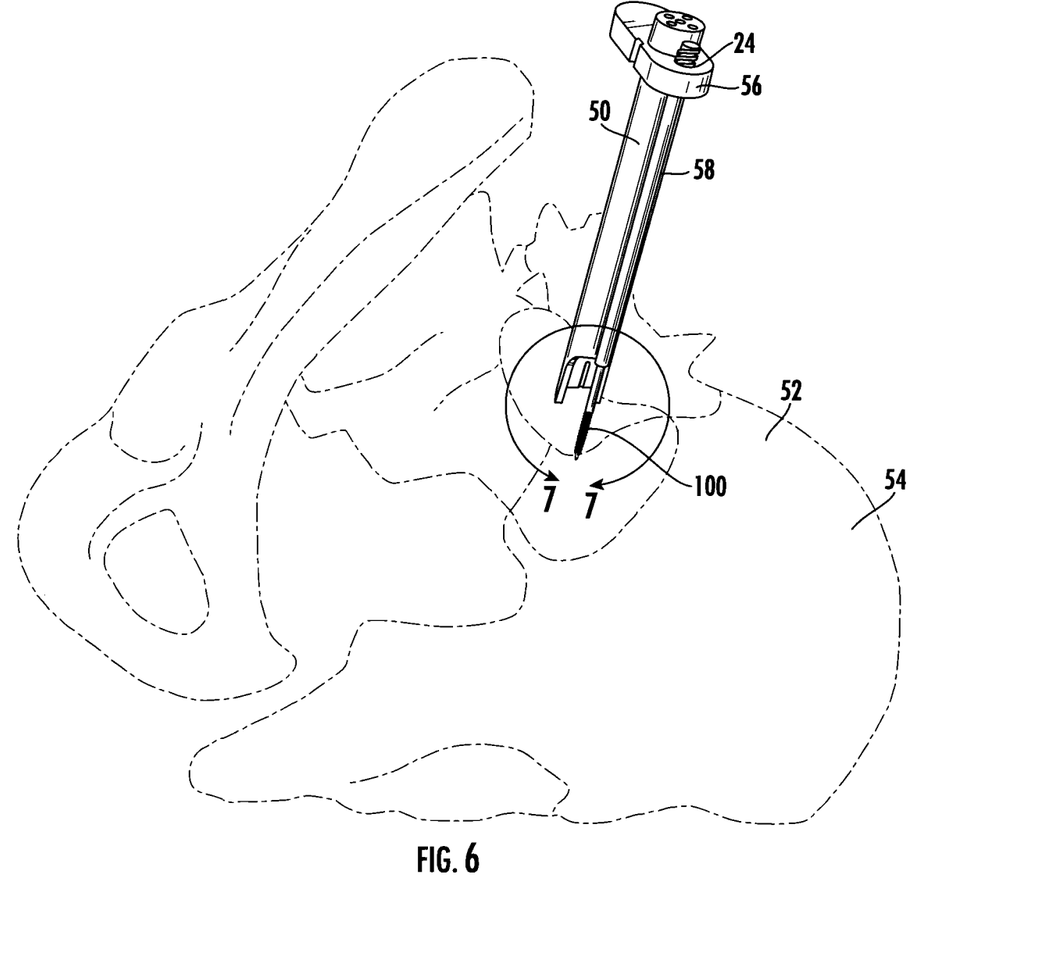
FIG. 6 is a perspective view, illustrating the fastening cannula securing a surgical fixture to a pelvis bone.
Figure 7:
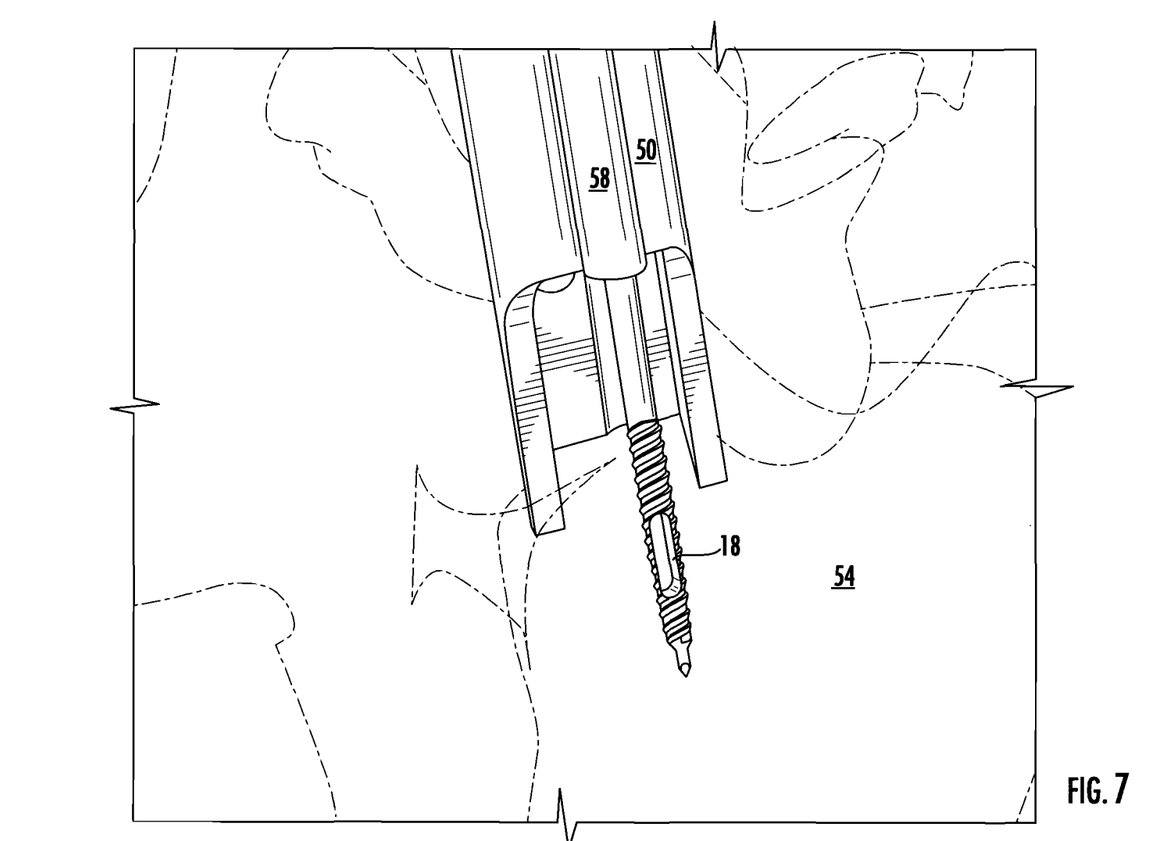
FIG. 7 is a partial view taken along lines 7-7 of FIG. 6, illustrating the directional aperture within the bone.
Figure 8:
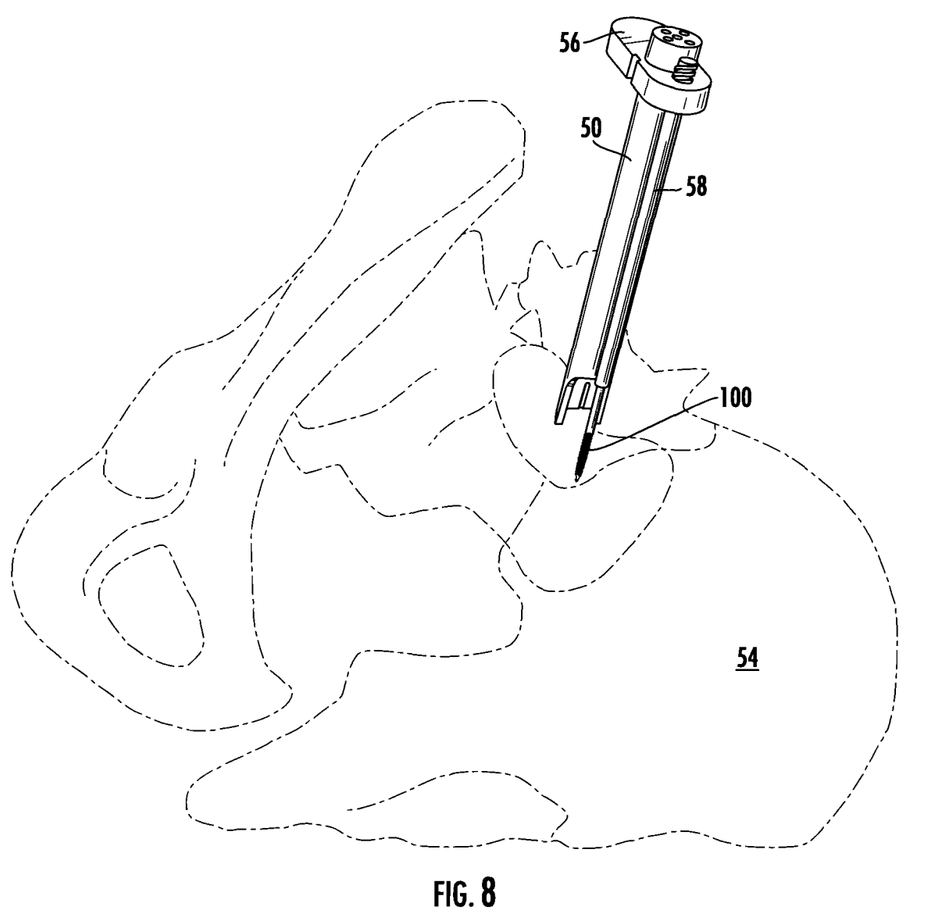
FIG. 8 is a perspective view, illustrating the connector on the distal end of the fastening cannula cooperating with a plate on a surgical drill fixture to secure the fixture in position.
Figure 9:
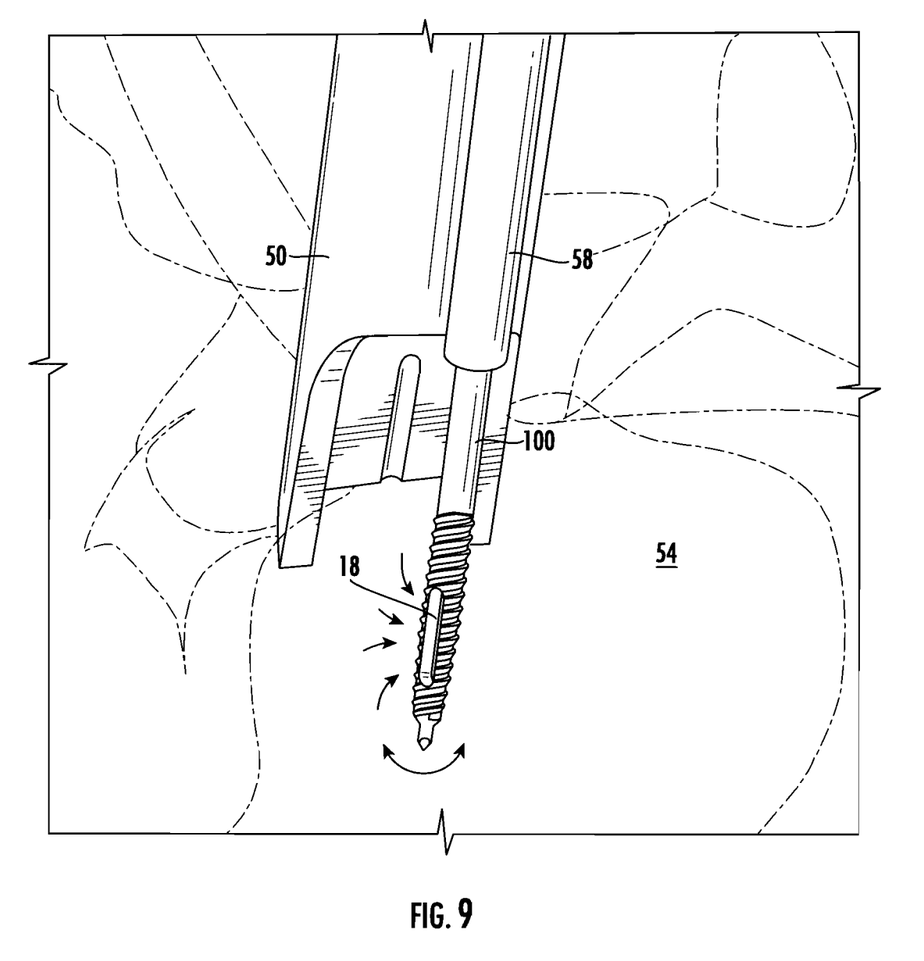
FIG. 9 is a partial perspective view, illustrating the directional aperture being utilized to draw in bone marrow.
Figure 10:
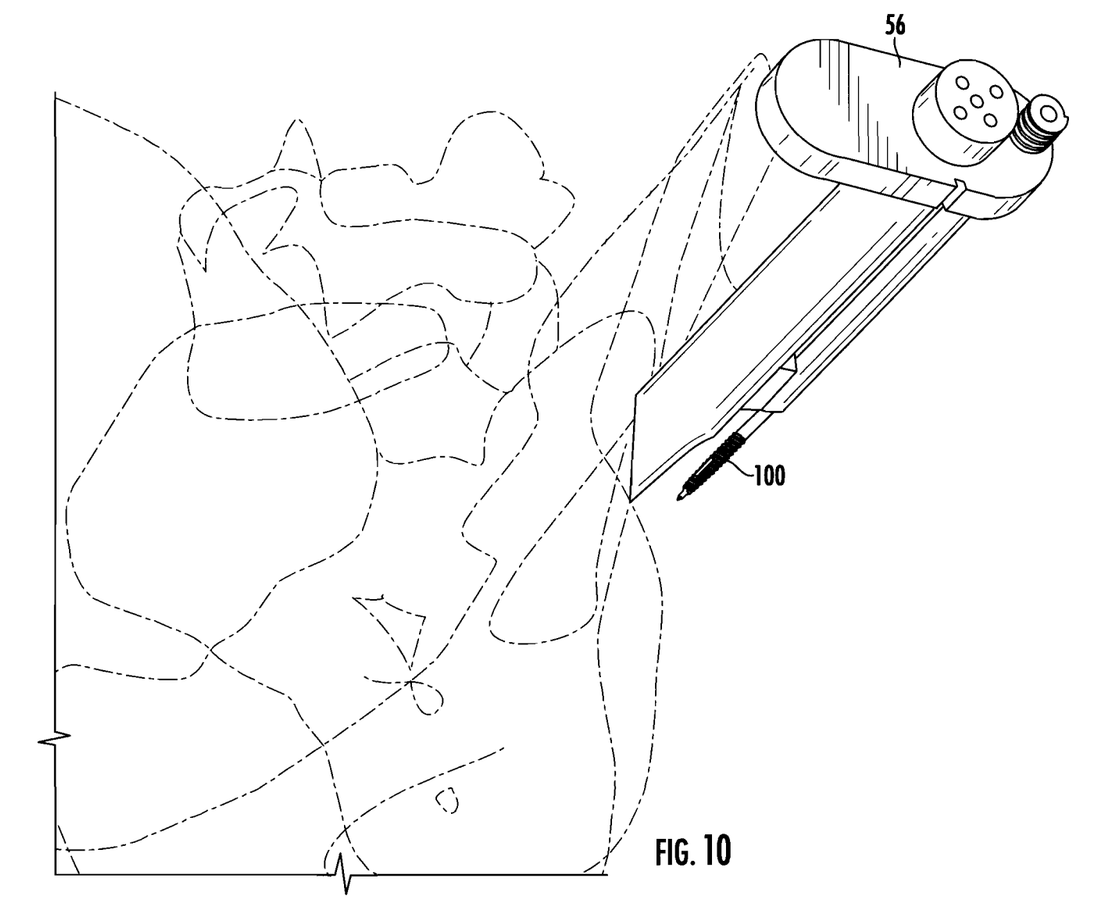
FIG. 10 is a perspective view, illustrating the fastening cannula securing the drill guide in place.
Figure 11:
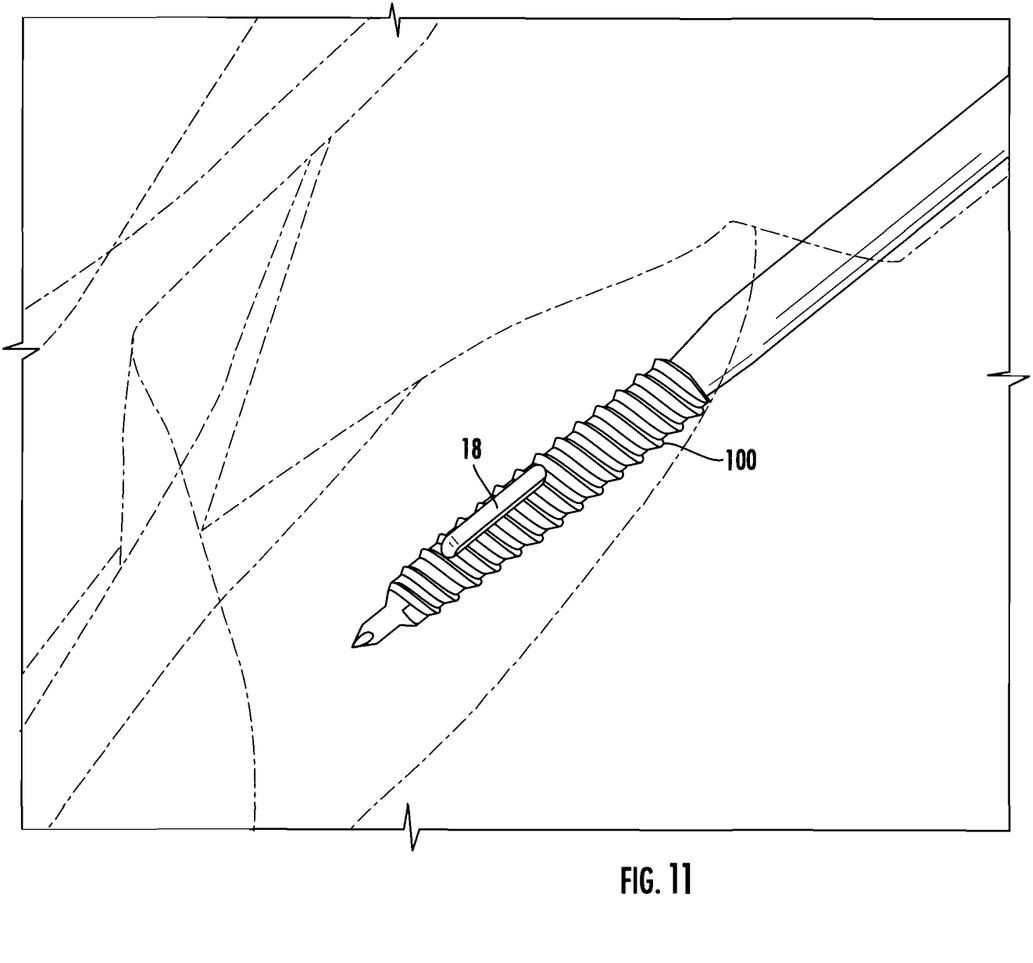
FIG. 11 is a partial perspective view, illustrating the directional aperture being utilized to draw in bone marrow.

FIG. 7 illustrates the position of the directional aperture 18 within the pelvis bone 54. Also illustrated is a tube 58 secured to the surgical fixture 50 to provide additional alignment between the cannulated fastener 100 and the surgical fixture 50.

Figure 12:
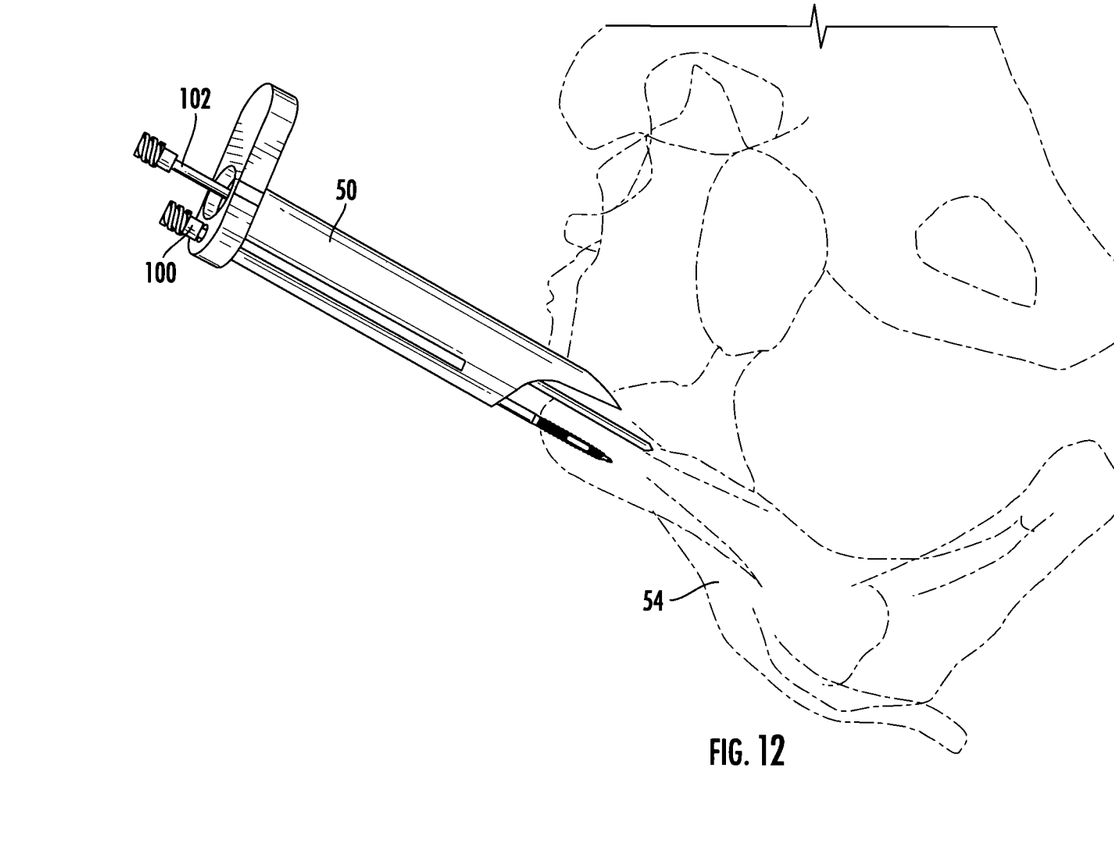
FIG. 12 is a perspective view, illustrating one cannulated fastener securing the drill fixture, while a second cannulated fastener is utilized to provide pilot holes for drill bits while simultaneously providing additional bone marrow from locations where marrow is not typically removed.
Figure 13:
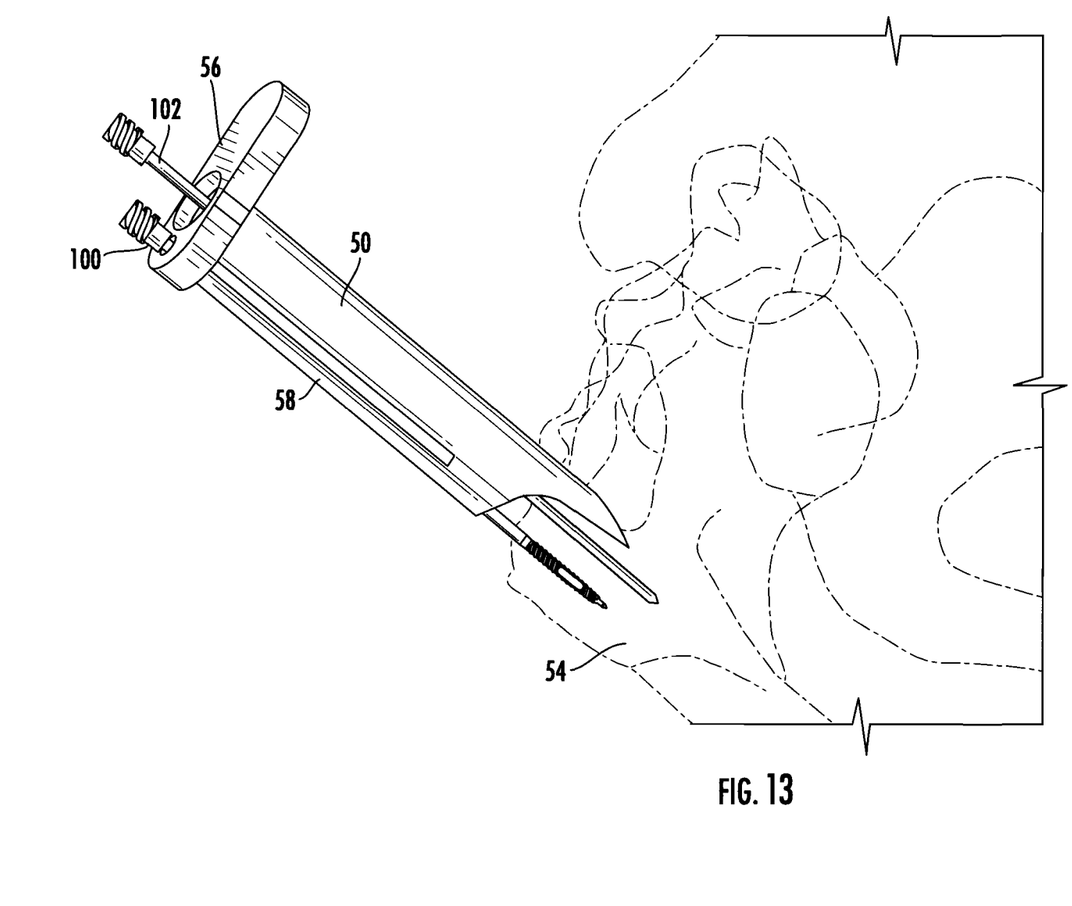
FIG. 13 is a perspective view of the multiple cannulated fasteners of FIG. 12.

FIGS. 12 and 13 illustrate multiple cannulated fasteners 100 in use in a single procedure. As shown, a first cannulated fastener 100 is used to secure the surgical fixture 50 in position, while a second cannulated fastener 102 is used to withdraw marrow through the surgical fixture 50 from an area that will be removed during the surgical procedure. In this manner, the present device can harvest bone marrow from an area where the marrow is typically lost to the procedure, providing a significant advantage to the patient who can utilize the marrow to enhance bone growth in the same area. Thus, a cannulated fastener 100, 102 has been shown, and its method of use explained, while several advantages of its use have been described.

What is claimed is:

1. A cannulated fastener for surgical procedures comprising:

said cannulated fastener (100) including a first end (10), a sidewall, and a cannula bore, said first end (10) being closed and including a drill point (14), said drill point (14) including a center point (28) positioned along a longitudinal centerline of said cannulated fastener (100), a tapered lead (16), said tapered lead (16) being smooth and free from cutting surfaces and extending between said drill point (14) and a holding surface (11), said tapered lead constructed and arranged to expand and size a diameter of a hole in a bone formed by the drill point (14) by smoothing or burnishing sidewalls of the hole, said holding surface constructed and arranged to cooperate with the sidewalls of the hole to compressively form a portion of the sidewalls of the hole to secure the cannulated fastener to the bone and a directional aperture (18) extending through the sidewall of said cannulated fastener (100) to provide a fluid connection to the cannula bore (36) of said cannulated fastener (100);

a second end (20) including a connector (22) for connecting to a source of vacuum, whereby vacuum is applied to said cannula bore (36) and said directional aperture (18) for drawing bone marrow aspirate from a hole in a bone created by said cannulated fastener (100).

2. The cannulated fastener of claim 1 wherein said holding surface (11) comprises helical threads (12).

3. The cannulated fastener of claim 1 wherein said holding surface (11) includes threads (12), which are constructed and arranged to form conjugate threads in a bone by compression of bone material.

4. The cannulated fastener of claim 3 wherein said threads (12) are at least double helix threads, each said additional helix providing insertion into a bone with fewer rotations of said cannulated fastener (100).

5. The cannulated fastener of claim 1 wherein said connector (22) is constructed of plastic overmolded to said second end (20) of said cannulated fastener (100) to create an airtight connection therebetween.

6. The cannulated fastener of claim 5 wherein said connector (22) includes a Luer lock connection (38) for connection to a source of vacuum.

7. The cannulated fastener of claim 5 wherein said connector (22) includes a shoulder (24) arranged to be substantially perpendicular to said cannula bore (36), said shoulder (24) constructed and arranged to contact an adjacently placed surface of a surgical fixture (50) to retain said fixture's positioning with respect to a bone.

8. The cannulated fastener of claim 7 including a spacer zone (26) configured to be positioned between said shoulder (24) and a source of vacuum to allow said vacuum source to be connected to said Luer lock connection (38) for bone marrow aspirate extraction, while said shoulder (24) is simultaneously utilized to retain a surgical fixture (50).

9. The cannulated fastener of claim 7, wherein said cannula (36) is constructed from stainless steel.

10. The cannulated fastener of claim 1 wherein said drill point (14) is a moil drill point (14) said moil drill point (14), having a center point (28) and multiple sharp edges (30).

11. The cannulated fastener of claim 6, wherein said Luer lock connection (38) also includes threads (40).

12. The cannulated fastener of claim 1 wherein said drill point (14) is a split drill point.

13. The cannulated fastener of claim 1 wherein said drill point (14) is a spade drill point.

14. The cannulated fastener of claim 1 wherein said holding surface (11) includes knurling.

15. The cannulated fastener of claim 1 wherein said holding surface (11) includes annular rings.

16. The cannulated fastener of claim 1 wherein said holding surface (11) includes a rougher surface finish than the remainder of said cannula.

17. The cannulated fastener of claim 1 wherein said holding surface (11) includes a coating to create a surface finish.

* * * * *